US006858209B2

(12) United States Patent
Klein et al.

(10) Patent No.: US 6,858,209 B2
(45) Date of Patent: Feb. 22, 2005

(54) **MEANS FOR DETECTING BACTERIA OF THE *TAYLORELLA EQUIGENITALIS* SPECIES AND THEIR BIOLOGICAL APPLICATIONS**

(75) Inventors: Frédéric Klein, Alençon (FR); Dragos Gradinaru, Alençon (FR)

(73) Assignee: Conseil General de l'Orne (FR)

( * ) Notice: Subject to any disclaimer, the term of this patent is extended or adjusted under 35 U.S.C. 154(b) by 0 days.

(21) Appl. No.: 09/155,982

(22) PCT Filed: Apr. 11, 1997

(86) PCT No.: PCT/FR97/00649

§ 371 (c)(1),
(2), (4) Date: Oct. 9, 1998

(87) PCT Pub. No.: WO97/39034

PCT Pub. Date: Oct. 23, 1997

(65) Prior Publication Data

US 2002/0037879 A1 Mar. 28, 2002

(30) Foreign Application Priority Data

Apr. 12, 1996 (FR) .............................................. 96 04623

(51) Int. Cl.[7] ...................... A01N 57/00; A61K 31/665; A61K 39/395; A61K 48/00
(52) U.S. Cl. ................. 424/164.1; 424/150.1; 424/185.1; 424/234.1; 424/256.1; 424/243; 424/93.1; 435/7.32; 530/300; 530/388.1; 530/387.1; 514/2; 514/8; 514/12; 514/100; 514/23; 514/54; 422/61
(58) Field of Search ........................ 424/185.1, 150.1, 424/234.1, 164.1, 256.1, 243, 93.1, 180; 435/7.32, 7.1; 530/300, 388.1, 324, 387.1, 388.2; 514/2, 8, 12, 100, 23, 54; 422/61

(56) References Cited

U.S. PATENT DOCUMENTS

| 4,444,879 A | * | 4/1984 | Foster .......................... 435/7 |
| 4,483,851 A | * | 11/1984 | Swerczek ..................... 514/23 |
| 4,540,660 A | * | 9/1985 | Harte et al. .................... 435/7 |
| 4,600,711 A | * | 7/1986 | Swerczek ..................... 514/23 |
| 5,891,438 A | * | 4/1999 | Silverman ................ 424/185.1 |

FOREIGN PATENT DOCUMENTS

WO      WO 86/02360      4/1986

OTHER PUBLICATIONS

English Transllation of Akuzawa, N et al, Nippon Jui Gakkai Koen Yoshshu, vol. 121, p. 143, 1996.*
Corbel, MJ et al, J. Hyg., Dec. 1982, vol. 89(3), pp. 529–538.*
Fischer, Gerald W.,.New Topics in Pediatric Infectious Disease, 1988, pp. 517–533.*
Friedrich, U, Pferdeheilkunde, 1995, vol. 11(1), Jan.–Feb., p. 13, Examination on the relationship between the pathogen germ and its host in the case of *Taylorella equigenitalis* infection of stallions and the development of monoclonal antibodies used in di.*

(List continued on next page.)

*Primary Examiner*—Lynette R. F. Smith
*Assistant Examiner*—Ginny Allen Portner
(74) *Attorney, Agent, or Firm*—Burns, Doane, Swecker & Mathis, L.L.P.

(57) ABSTRACT

Means for detection of bacteria of the genus *Taylorella* and biological applications thereof are described. In particular, the detection of *T. equigenitalis* and the treatment or prevention of infections caused by bacteria of this species are disclosed. Monoclonal antibodies which recognize an epitope of a bacterium of the species *T. equigenitalis* are disclosed. These monoclonal antibodies may be used to detect *T. equigenitalis* with certainty and by means of a single test.

38 Claims, 2 Drawing Sheets

OTHER PUBLICATIONS

Figure 1:
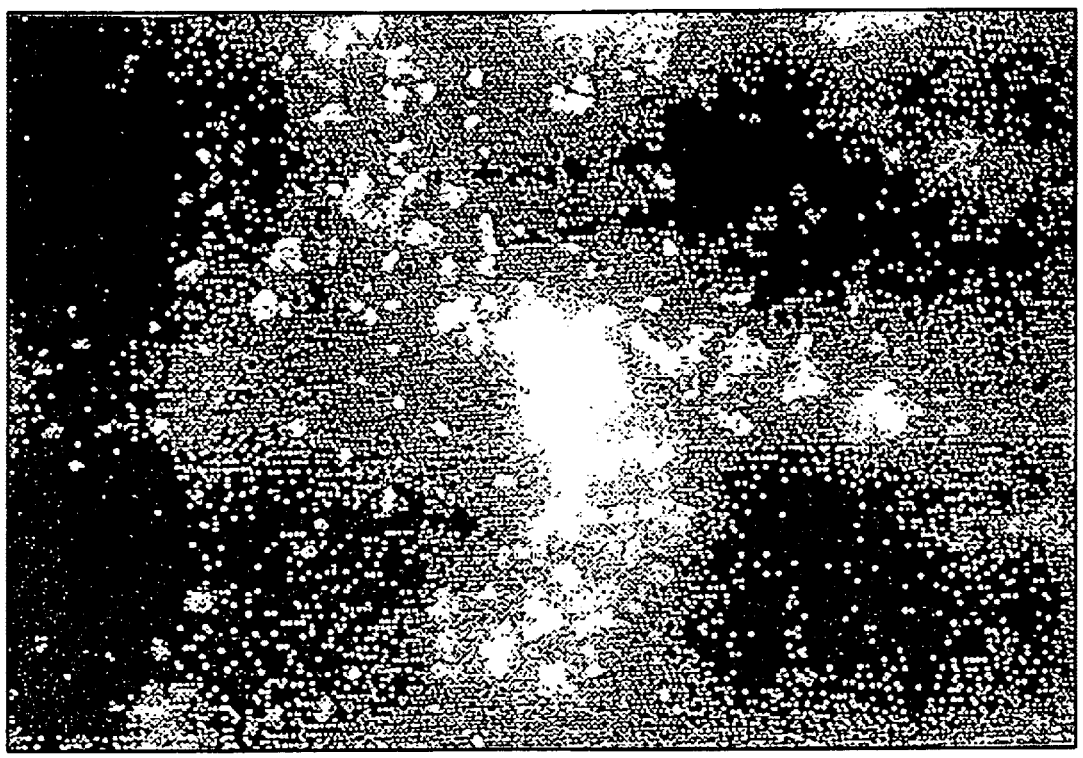

Sugimoto, C et al, Isolation and characterization of the outer membrane of *Taylorella equigenitalis*, Conference Title, Equine Infectious diseases V: Proceeding of the fifth international conference, pp. 164–167, 1988, editors: Powell, D.G..*

Tainturier, DJ et al, J. Clinical Microbiology, vol. 14(4), pp. 355–360, Oct. 1981.*

Harlow et al, Monoclonal Antibodies: A Laboratory Manuel, 1998, specific pages.*

Akuzawa et al, Manufacture of monoclonal antibody against bacterial outermembrane of *Taylorella equigenitalis*, Nippon Vet. and Anim. Sci. Univ., Nippon Jui Gakkai Koen Yoshishu, 1996, vol. 121, p. 143, English translation (abstract).*

Lin, YS et al, Journal of Medical Microbiology, vol. 27(4), pp. 263–270, 1988, Production and characterization of monoclonal antibodies for staphylococcal enterotoxin B, abstract only.*

Boslego, John W. et al, Chapter 17, Gonorrhea vaccines, pp. 211–223, In Vaccines and Immunotherapy, 1991, Pergamon Press, Edited by Stanley J. Cryz, Jr.b.*

Sugimoto, C. et al, (abstract), Equine infectious diseases, V:Proceedings of the fifth international Conference, pp. 164–167, 1988.*

Fredrich, U.m (abstract), Pferdeheilkunde, 1995, vol. 11(1), Jan.–Feb., p. 13.*

Guerin, B. Fecueil De Medecine Veterinarie, (abstract) 1992, vol. 168(N11-1), pp. 1029–1043.*

Noriko, A. et al, Nippon Jui Gakkai Koen Yoshishu, (abstract), vol. 121, p. 143, 1996.*

McBeath, D. G. et al, Equine veterinary Journal, vol. 15(3), pp. 196–202, 1983.*

Youngquist, R.S. et al, Am. J. Vet. Res, vol. 44(8), pp. 1405–1409, 1983.*

Widders, P.R. et al, Research in Veterinary Science, vol. 40(1), pp. 54–58, 1986.*

Friedrich, U; Pferdeheilkunde, vol. 11(1), Jan.–Feb., p. 13, 1995.*

Akuzawa, N et al, Nippon Vet and Animal. Science University, Nippon Jui Gakkai Koen Yoshishu, vol. 121, p. 143, vol. 121, 1996.*

Tainturier, D.J. et al, Journal of Clinical Microbiology, Oct. vol. 14(4), pp. 355–360, 1981.*

Corbel, MJ et al; J. Hyg. (London, England), Dec. vol. 89(3), pp. 529–538, 1982.*

Sugimoto, C et al, Equine Infectious diseases V:proceeding of the fifth International Conference, pp. 164–167, 1988.*

Harlow et al; Monoclonal Antibodies: A Laboratory Manuel; Cold Spring Harbor Press, Chpts 6, 9, 14(15); 1988.*

A.P. MacMillan et al, Antibodies Reactive with *Taylorella equigenitalis* In Equine Sera, 1986, *The Veterinary Record* 118: 562.

Masashi Eguchi et al., Passive Hemagglutination Test for Detection of Antibodies Against *Taylorella* (*Haemophilus*) *equigenitalis* in Sera of Mares, 1988, *Veterinary Microbiology*, 18: 155–161.

D.A. Gradinaru et al, Production and Characterization of Monoclonal Antibodies Against *Taylorella equigenitalis*, 1997, *Vet. Res.*, 28: 65–76.

* cited by examiner

MEANS FOR DETECTING BACTERIA OF THE *TAYLORELLA EQUIGENITALIS* SPECIES AND THEIR BIOLOGICAL APPLICATIONS

CROSS REFERENCE TO RELATED APPLICATIONS

The instant application claims priority under 35 U.S.C. §371 to PCT Application No. PCT/FR97/00649, filed Apr. 11, 1997, and under 35 U.S.C. §119 to French Application No. 96/04623, filed Apr. 12, 1996.

FIELD OF THE INVENTION

Means for detection of bacteria of the genus *Taylorella* and biological applications.

The invention relates to means for the detection of bacteria of the genus *Taylorella* and their biological applications.

It relates in particular to the detection of *T. equigenitalis* and the treatment or prevention of infections caused by bacteria of this species.

BACKGROUND OF THE INVENTION

The first strain of *T. equigenitalis* was isolated by Crowhurst, 1977, Vet. Rec. 100, 476 and characterized by Taylor et al., 1978, Equine Vet. J. 10, 136–134. This bacterium is the agent of a venereal disease of the Equidae called contagious equine metritis (designated CEM hereinafter).

Since the first appearance of this disease in 1977 at Newmarket (Great Britain), CEM has spread among the world's equine population (Europe, USA, Japan).

CEM was initially characterized by the appearance of purulent vaginal discharges caused by acute endometritis. The epidemiology and the clinical signs of the disease have now changed. Very few foci remain, exhibiting an acute form of CEM; it is then a question of contamination of several mares in the same harem. Clinical forms of metritis have in fact become rare, and *T. equigenitalis* is mainly found in asymptomatic carriers or at the preclinical stage. The disease is transmitted by stallions that do not show any clinical symptom.

CEM constitutes an obstacle to the international exchange of Equidae and its screening is recommended by the IEO (International Office of Epizootics), list B).

Indirect screening means such as serology have been abandoned by numerous countries such as the USA, Great Britain and France.

Direct screening means are implemented: screening by bacteriological culture in numerous countries, screening by indirect immunofluorescence.

In France, prophylactic measures comprise both bacteriological culture and indirect immunofluorescence (IIF).

Systematic screening of stallions has become mandatory prior to each mating season.

For economic and management reasons, this systematic screening can only be done from one or two samples per animal and per season. The reliability of this screening is therefore even more crucial.

The screening test for infection by *T. equigenitalis* currently employed in France is based mainly on isolation of the bacterium by culture on nutrient and/or selective media and on the identification of this agent according to morphologic and biochemical criteria. However, *T. equigenitalis* is a very fragile and very slow-growing bacterium (the observation time of the culture dishes is at least 6 days). Furthermore, it is liable to be inhibited by other bacteria of the flora examined. The criteria for identifying the various strains of *T. equigenitalis* are themselves either too succinct and liable to variations (demonstration of absence of activity for the three classical enzymatic activities exhibited by *T. equigenitalis*), or too extensive to be managed in the required time. Detection by the bacteriologic technique alone has therefore become a hazardous method of diagnosis. An indefinite percentage of healthy carriers is thus regarded as uninfected each season.

A second test for detecting infection by *T. equigenitalis* has been adopted in France. This test is based on identification of the bacterium by indirect immunofluorescence using antiserum made in the rabbit and fluorescent anti-rabbit antibodies. This assay has the advantage that it delivers its results much more quickly (24 to 48 hours) than an assay by bacteriologic culture.

Application of this technique can, however, lead to errors through excess (false positives), as in many cases the antisera used give rise to reactions with species other than *T. equigenitalis.*

The significance of these results is thus very limited: if the immunofluorescence assay is negative, the registered laboratory may report a negative conclusion, but if the result is positive, this result must be either confirmed or invalidated by bacteriology.

The inventors tried to rectify these difficulties in the detection of infection by *T. equigenitalis*, by elaborating new means for identifying a bacterium of the species *T. equigenitalis* without risk of false positives or of false negatives. The present invention also offers advantages of speed and simplicity of execution.

BRIEF SUMMARY OF THE INVENTION

The invention therefore aims to provide means for very reliable, specific detection of *T. equigenitalis*, based on recognition of a defined antigen-antibody type.

It also relates to the use of these means for the diagnosis, treatment and prevention of diseases caused by *T. equigenitalis.*

According to a first aspect, these means of the invention are monoclonal antibodies characterized in that they recognize an epitope of a bacterium of the species *T. equigenitalis.*

Advantageously, these antibodies do not exhibit crossed reactions with an epitope or epitopes of a *Taylorella* bacterium of a different species or of a bacterium of a different genus. They therefore make it possible to detect *T. equigenitalis* with certainty and, according to a very interesting embodiment, by means of a single test.

The monoclonal antibodies of the invention (abbreviated to AcM hereinafter) are also those obtained starting from hybrids, by fusion of non-secreting murine myeloma cells with spleen cells obtained from mice immunized using an inactivated strain of the species *T. equigenitalis* or extract(s) of such a strain, cloning and selection according to the ability of their culture supernatant to recognize one or more epitopes of a bacterium of the species *T. equigenitalis*, and recovery of the required antibodies, followed if necessary by their purification.

The invention also relates to fragments of the AcM defined above, more particularly their Fv, Fab, F(ab') 2 fragments.

The AcM of the invention and, if appropriate, their fragments, are further characterized in that they are capable of recognizing proteins of *T. equigenitalis* from the group comprising proteins such as proteins of 150, 120, 52.7 or 22 (LPS) kDa.

According to a second embodiment, the means of the invention are immunogenic proteins characterized in that they are capable of interacting with the said AcM or their fragments.

These proteins are obtained, thanks to the said AcM or their fragments, from *T. equigenitalis*, or by synthesis.

According to a third embodiment, the means of the invention are anti-antibodies (abbreviated hereinafter to anti-AcM) and the fragments of these anti-antibodies, these anti-AcM and their fragments being characterized in that they are capable of interacting with the AcM or their fragments defined above.

The invention also relates to methods of obtaining the means defined above.

To produce the AcM of the invention, or the anti-AcM, it is also advantageous to employ the technique of obtaining hybridomas such as described by Kohler and Milstein in Nature 1975, 256, 495–497.

The invention thus relates to a method of production and selection of the AcM defined above, characterized in that it comprises:

fusion of non-secreting murine myeloma cells with spleen cells from mice immunized using a strain of the species *T. equigenitalis* or extract(s) from such a strain, screening by means of a detection technique, such as, especially, indirect immunofluorescence, of hybridomas whose culture supernatants exhibit a positive reaction with a bacterium of the species *T. equigenitalis* or a fragment of the latter, cloning of these hybridomas, with respect to their reactivity in relation to *T. equigenitalis*, and recovery of the AcM required, followed if necessary by their purification.

The invention also relates to the application of the above technique for the production of anti-AcM antibodies.

BRIEF DESCRIPTION OF THE DRAWINGS

FIG. 1 shows a photograph of an IIF (indirect immunofluorescence) assay on *T. equigenitalls* in the presence of AcM according to the invention.

FIG. 2 shows a photograph of an immunoblot after reaction of proteins of *T. equigenitalis* with AcM of the invention and immunized mouse serum (positive serum).

FIG. 3 shows a photograph of a dot blot carried out on the non-denatured proteins of a reference strain of *T. equigenitalis* and incubated with the AcM according to the invention, a positive mouse serum (SP) or a negative mouse serum (SN) (un-immunized mouse).

DETAILED DESCRIPTION OF THE INVENTION

Spleen cells from mice previously immunized using the AcM already defined are used in this case. The cloned strains can be preserved in liquid nitrogen and their culture supernatants at −20° C. These strains, which are characterized by the fact that they are capable of producing AcM or anti-AcM respectively, as defined above, also fall within the scope of the invention. In general, the invention relates to strains of hybridomas such as obtained according to the methods defined above.

The fragments of the AcM and the anti-AcM can easily be obtained using conventional enzymatic techniques.

With the three embodiments defined above, namely the AcM or their fragments, the immunogenic proteins, and the anti-AcM or their fragments, the invention provides the means for establishing, either directly or indirectly, eventual contamination of a sample or of a culture with a bacterium of the species *T. equigenitalis.*

Within the scope of such a determination, the invention relates to a method of identifying a bacterium of the species *T. equigenitalis* or of one or more epitopes of such a bacterium in a sample or in a culture, characterized in that it comprises:

bringing the sample or the culture to be analysed, which may contain *T. equigenitalis*, into contact with i. an effective quantity of at least one AcM or one fragment of AcM as defined above and, optionally, blocking non antigen-antibody reactions, for example by saturation of the sample or of the culture to be analyzed using a serum, such as mouse serum, from which anti-*T. equigenitalis* antibodies have been removed, ii. or as a variant, for demonstrating the presence of antibodies directed against *T. equigenitalis*, with an effective quantity of an immunogenic protein or anti-AcM antibody, or of fragments of the latter, as defined above, under conditions allowing a reaction of the antigen-antibody type, and detection of any antigen-antibody type reaction product formed.

The contact stage is carried out in conditions especially of duration, temperature, and buffer, permitting establishment of an antigen-antibody type of reaction. Markers are used for detection, for example fluorescent, enzyme, radioactive or luminescent markers.

It should be noted that judicious choice of a particular AcM, or of a fragment of this AcM, permits direct identification of a given epitope of *T. equigenitalis* in a sample or a culture to be analysed. Use of an immunogenic protein or an anti-AcM antibody or a fragment of the latter will reveal previous contact of the sample or of the culture with the bacterium.

The absence of cross reactions of the AcM of the invention and of their fragments with epitopes of bacteria of the genus *Taylorella* other than *T. equigenitalis*, and of bacteria of a different genus, is utilized advantageously for the diagnosis of pathologies associated with *T. equigenitalis.*

The invention therefore also relates to the use of the said AcM and their fragments for the diagnosis of an infection by *T. equigenitalis*, and more particularly of contagious equine metritis, characterized in that it comprises:

the bringing of one or more AcM of the invention, or of their fragments, into contact with a biological sample, and detection of the antigen-antibody type of reaction produced when *T. equigenitalis* is present in the sample, and, optionally, the blocking of the non antigen-antibody reactions, for example, by saturation of the collected sample using a serum, such as mouse serum, from which anti-*T. equigenitalis* antibodies have been removed.

The stages of bringing into contact and detection are employed advantageously as indicated for the preceding method.

The invention also provides kits for application of the methods of identification and methods of diagnosis described above.

These kits are characterized in that they contain one or more AcM or their fragments or at least one immunogenic protein, or one or more anti-AcM or their fragments, reagents, in particular markers or buffers, for detecting the intended immunologic reaction, and, optionally, reagents for blocking non antigen-antibody reactions such as mouse serum, as well as instructions for use.

According to another advantageous embodiment of the invention, the AcM and their fragments defined above can be used therapeutically for combating an infection by *T. equigenitalis*, and more particularly against contagious equine metritis.

The invention thus also relates to pharmaceutical compositions containing one or more AcM, or their fragments, defined above, as vectors of medication or as agents of passive immunotherapy, alone or in conjunction with pharmaceutically inert vehicles. It also relates to their use for the production of biosensors.

According to yet another embodiment, the invention relates to the use of immunogenic proteins and anti-AcM or their fragments for the preparation of vaccinal compositions for preventing infection by *T. equigenitalis*.

The vaccinal compositions of the invention are characterized in that they contain at least one immunogenic protein or one anti-AcM or their fragments, as defined above, in sufficient quantity to produce an immune response, in combination with physiologically acceptable excipients.

Other characteristics and advantages of the invention will be given in the examples that follow.

EXAMPLES

Example 1

Production and Selection of Hybridomas Capable of Producing anti-*T. equigenitalis* Monoclonal Antibodies strains of *T. equigenitalis* used for immunization The results obtained with the following nine strains are reported:

two reference strains (R1-16 and R2-19), originating from the National Veterinary and Foodstuffs Research Centre—Central Laboratory for Veterinary Research (CNEVA-LCRV), Maisons-Alfort, France, seven strains called wild-type strains, isolated in four different regions in the north-west of France (Indre et Loire, Calvados, Côtes d'Armor and Orne), These strains are identified below in Table I:

TABLE I

| Designation of the strain | Sources | Resistance to streptomycin |
|---|---|---|
| R1-16/16 | CNEVA | S |
| R2-19/19 | CNEVA | R |
| 1/129S | LVD37 | R |
| 2/1 | LVD14 | R |
| 3/12.397 | LDA22 | R |
| 4/26.658 | LDA22 | R |
| 6/250 | LVD61 | R |
| 5/7001-01 | LDA22 | R |
| 7/715 | LVD61 | R |

S = sensitive
R = resistant

All of these strains are cultivated on chocolate agar with or without addition of actidione and streptomycin. They are incubated under a humid atmosphere at 7 $CO_2$.

Enzyme reaction analyses and sugar fermentation analyses are carried out using the API-NH system (BioMérieux, Marcy-l'Etoile, France).

In addition, these strains are tested or their catalase and cytochrome-oxidase activity and by the serum agglutination test (SAT), using a polyclonal rabbit serum.

Most of them have a Gram-negative coccobacillus form, catalase and cytochrome oxidase activity, and they respond positively to the SAT agglutination test.

It is found that they all exhibit positive alkaline phosphatase and gamma glutamyl transferase activity (except the strain from soil 5 which exhibits negative gamma glutamyl transferase activity), negative penicillinase, ornithine-decarboxylase, urease, lipase, beta-galactosidase and proline-amylase activities. It is also found that they do not metabolize sugars (glucose, fructose, maltose, saccharose).

Moreover, they have very similar polypeptide and lipopolysaccharide profiles.

The two reference strains R1-16 and R2-19 thus display the properties that are generally observed for all strains of *T. equigenitalis* investigated in the prior art and are therefore used for the immunization of mice.

Immunization of Mice

The reference strains R1-16 and R2-19 are washed twice in PBS buffer 0.1 M, pH 7.4 and inactivated by heating at 56° C. for 75 min. The cells are then diluted in PBS until bacterial suspensions are obtained with an optical density of 0.77 to 380 nm. They are then divided into aliquot portions and stored at −80° C. until use.

Adult BALB/C mice are injected intraperitoneally with 0.5 ml of R1-16 and R2-19 bacterial suspensions emulsified with Freund's complete adjuvant (2 mice per strain). A repeat injection is made on the 14th day with the same preparation. On the 21st day, the mice are immunized with 0.2 ml of suspension without adjuvant by intravenous route and the spleen cells are collected 2 days later.

Production of Hybridomas

Hybridomas are produced by the standard procedure described by Kohler and Milstein (see reference above).

SP2-0-Ag14 mouse myeloma cells and immune spleen cells are fused in a ⅕ ratio using PEG 1500 (Sigma, l'Isle d'Abeau, France) and kept in 96-well cell culture plates containing mouse macrophages or spleen nutrient cells or an OPI supplement (Sigma) in a HAT-DMEM (Hypoxanthine, Aminopterine and Thyrnidine-Dulbecco Minimum Essential Medium) selective medium.

Hybridoma growth is observed in 820 of the 1020 wells used (81.37%). The IIF tests are carried out on 60 of these 820 wells in order to detect the hybridomas producing the required monoclonal antibodies.

Screening of the Hybridomas and Monoclonal Antibodies Produced

The hybridomas are tested by indirect Immunofluorescence (IIF) for the ability of their supernatants to recognize the two reference strains of *T. equigenitalis*. The standard procedure described by Vaissaire et al. (1992), Bull. Acad. Vet. Fr. 65, 161–170 is used.

After washing twice in PBS 0.1 M, pH 7.4, the bacterial strains are resuspended in the PBS buffer containing, in addition, 1% of formaldehyde in order to obtain a suspension that has a turbidity of 1 on the MacFarland scale. 10 $\mu$l of this suspension is applied to each spot of the fluorescent strips.

After drying for 15 min at 37° C., the strips are fixed in pure acetone for 15 min at ambient temperature.

After drying, the strips are left to incubate with 40 µl of hybridoma supernatants for 30 min at 37° C.

The strips are then washed in a stirred bath of PBS for 15 min. After rinsing in distilled water and drying, the strips are incubated for 30 min at 37° C. with 40 µl of a solution of fluorescein isothiocyanate conjugated with rabbit anti-mouse fraction F (ab) 2 (Eurobio Les Ulis, France), diluted to 1/40 in PBS containing Evans blue 1/10000).

The strips are then washed in PBS, rinsed in distilled water, dried as indicated above, mounted in PBS containing 1% of glycerol and examined with a fluorescence microscope.

An un-immunized mouse serum is used as negative control. The mouse antiserum FITC conjugate is incubated with each bacterial strain to serve as a conjugated control.

The clones that are positive in the IIF test are transferred for expansion before cloning into 24-well plates containing HAT-DMEM medium.

FIG. 1 shows an IIF test on *T. equigenitalis* in the presence of AcM according to the invention. This figure shows strong fluorescence of the bacterial wall.

4 to 7 days later, the hybridomas from these wells are cloned by the method of limiting dilution in order to obtain a single cell per well in a 96-well tissue culture plate, using HT-DMEM medium and nutrient cells. The wells containing a single clone are screened by IIF and the positive cells are frozen in liquid nitrogen.

From the set of positive clones, 14 are used for the production of monoclonal antibodies and the characterization of these antibodies.

The supernatants of hybridoma tissue cultures are buffered by adding Tris 1 M, pH 8.0 (vol. 1/20) and sodium azide (0.02%). Aliquots are prepared and stored at −20° C.

Example 2

Characterization of the Anti-*T. equigenitalis* Monoclonal Antibodies

Specificity of the Monoclonal Antibodies

To verify the specificity of the monoclonal antibodies, the supernatants of the 14 hybridoma clones obtained according to Example 1 are tested by IIF with respect to the ability of their supernatants to recognize bacterial strains other than the two reference strains R-16 and R-19 used for immunization, namely:

the 7 wild-type strains of *T. equigenitalis* described in Example 1, and bacterial strains described in the prior art as giving rise to crossed reactions with the antisera of *T. equigenitalis* or commonly present in the genital flora: *Actinobacillus equuli, Pseudomonas aeruginosa, Pasteurella multocida, Pasteurella haemolytica, Streptococcus equi, Staphylococcus aureus, Pseudomonas fluoroscens* and *Klebsiella pneumoniae*. These bacteria are cultivated on a Columbia-base blood-agar medium.

The results obtained are presented in Table II below.

TABLE II

| No. | Designation of the AcM | R1-16 | R2-19 | 1 | 2 | 3 | 4 | 5 | 6 | 7 | Act equuli | Ps aeruginosa | P multo-cida | P haemolytica | Str equi | St aureus | Ps fluo-rescens | K pneu-moniae |
|---|---|---|---|---|---|---|---|---|---|---|---|---|---|---|---|---|---|---|
| 1 | 3B6.1 | + | + | + | + | + | + | + | + | + | − | − | − | − | − | − | − | − |
| 2 | 3B6.4 | + | + | + | + | + | + | + | + | + | − | − | − | − | − | − | − | − |
| 3 | 3B6.11 | + | + | + | + | + | + | + | + | + | − | − | − | − | − | − | − | − |
| 4 | 7B7.1 | + | + | + | (+) | + | + | + | + | + | − | − | − | − | − | − | − | − |
| 5 | 7B7.10 | + | + | + | + | (+) | (+) | + | + | + | − | − | − | − | − | − | − | − |
| 6 | 7B8.1 | + | + | + | + | + | + | + | + | + | − | − | − | − | − | − | − | − |
| 7 | 7C4.10 | + | + | + | + | + | + | + | + | + | − | − | − | − | − | − | − | − |
| 8 | 7D7.3 | + | + | + | + | + | + | + | + | + | − | − | − | − | − | − | − | − |
| 9 | 7D7.16 | + | + | + | + | + | + | + | + | + | − | − | − | − | − | − | − | − |
| 10 | 10C4.17 | + | + | + | + | + | + | + | + | + | − | − | − | − | − | − | − | − |
| 11 | 10C9.6 | + | + | + | + | (+) | (+) | + | + | + | − | − | − | − | − | − | − | − |
| 12 | 11C9.1 | + | + | + | + | + | + | + | + | + | − | − | − | − | − | − | − | − |
| 13 | 11C9.4 | + | + | + | + | + | + | + | + | + | − | − | − | − | − | − | − | − |
| 14 | 11C9.5 | + | + | + | + | + | + | + | + | + | − | − | − | − | − | − | − | − |

+ positive; (+) weak-positive; − negative

The 14 monoclonal antibodies tested recognize the seven wild-type strains of *T. equigenitalis*. Three of them give a more weakly positive response, namely 7B7.1; 7B7.10 and 10C9.6.

None of the 14 monoclonal antibodies tested recognizes one of the 8 bacterial strains that do not belong to the species *T. equigenitalis*.

These results demonstrate the specificity of the 14 monoclonal antibodies tested for the strains of *T. equigenitalis* and the absence of crossed reactivity between *T. equigenitalis* and other bacteria that do not belong to the species *T. equigenitalis*, and, either having been described with the tools of the prior art as exhibiting crossed reactivity with this species (*Actinobacillus equuli, Pasteurella multocida, Pasteurella haemolytica, Staphylococcus aureus, Pseudomonas fluorescens*) or forming part of the regular genital flora (*Streptococcus equi, Klebsiella pneumoniae, Pseudomonas aeruginosa*).

The positive reactions of the rabbit polyclonal antiserum observed in IIF with *Staphylococcus aureus* and *Psudomonas fluorescens* therefore were not observed with the monoclonal antibodies of the invention.

The monoclonal antibodies that are the subject of the present Application do not detect an antigenic difference between the various strains of *T. equigenitalis* tested.

SAT (Serum Agglutination Test)

Only strain R-19 was used for testing the reactivity of the monoclonal antibodies in the SAT.

The results obtained are given in column 4 of Table III below.

13 of the 14 monoclonal antibodies give a positive response.

TABLE III

| No. | Designation of the AcM | IIF | SAT | Immunoblot | Dot blot with denaturation | Dot blot without denaturation | Monoclonal specificity (kDa) | Isotype |
|---|---|---|---|---|---|---|---|---|
| 1 | 3B6.1 | + | + | + | + | + | 150 | IgM |
| 2 | 3B6.4 | + | + | − | − | + |  | IgM |
| 3 | 3B6.11 | + | + | − | − | + |  | IgM |
| 4 | 7B7.1 | + | − | − | − | + |  | IgG1 |
| 5 | 7B7.10 | + | + | + | + | + | 22 (LPS) | IgG1 |
| 6 | 7B8.1 | + | + | + | + | + | 52.7 | IgG3 |
| 7 | 7C4.10 | + | + | + | + | + | 52.7 | IgG3 |
| 8 | 7D7.3 | + | + | + | + | + | 22 (LPS) | IgM |
| 9 | 7D7.16 | + | + | − | − | + |  | IgM |
| 10 | 10C4.17 | + | + | − | − | + |  | IgG3 |
| 11 | 10C9.6 | + | + | − | − | + |  | IgG2b |
| 12 | 11C9.1 | + | + | + | + | + | 120 | IgG2b |
| 13 | 11C9.4 | + | + | + | + | + | 22 (LPS) | IgG2b |
| 14 | 11C9.5 | + | + | + | + | + | 22 (LPS) | IgG2b |

Localization of Specific Epitopes Preparation of Protein and Lipopolysaccharide Extracts of Strain R-19 of *T. equigenitalis*

Extraction in non-denaturing Conditions (EN) of *T. equigenitalis*

The cells of *T. equigenitalis* were collected by centrifugation (6000 g, 10 min) and washed three times in a solution of PBS 0.1 M at pH 7.4. The pellets were resuspended in a small volume of SDS buffer (sodium dodecyl sulphate at 2%, PBS pH=7.4) and incubated at 37° C. for 30 min. After this operation, the proteins still have their biological activity. After extraction in the SDS buffer, the integrity of the cells was checked by observations in phase-contrast microscopy. After centrifugation (10000 g, 10 min), the supernatants containing EN were completely dialysed against distilled water at 4° C. for 48 h, divided into aliquots and stored in the frozen state (−80° C.) until use. The concentration of EN proteins was determined using the BioRad protein test (BioRad, Ivry-sur-Seine, France).

Extraction in Denaturing Conditions ED

The EN extracts from the strains of *T. equigenitalis* were dissolved in a sample solvent (Tris.HCl 0.1 M pH 6.8; glycerol 10%; SDS 2%; β-mercaptoethanol 2 mM and bromophenol blue 0.01%) in order to obtain a protein concentration of 1 mg/ml, and were then boiled at 100° C. for 5 min (extract in denaturing conditions of *T. equigenitalis*, referred to herein as ED).

Lipopolysaccharide Extract (LPS)

EN extracts digested by proteinase K were used as LPS extracts (Hanner et al, 1991 Am. J. Vet. Res. 52, 1065–1068). 10 μl of EN was diluted in 35 μl of digestion buffer for LPS. This digestion buffer for LPS consists of 0.0625 M Tris.HCl pH 6.8; 0.1% SDS; 10% glycerol and 5 μg of proteinase-K (Sigma). These preparations were incubated at 57° C. for 1 hour and heated at 100° C. for 5 min before electrophoresis.

Sodium Dodecylsulphate Polyacrylamide Gel Electrophoresis (SDS-PAGE)

A batch-type SDS-PAGE electrophoresis (Laemmli, 1970, Nature, 227, 680–685) was used for separating the bacterial proteins. The separation gel contained 12% acrylamide and the staking gel contained 4% acrylamide. 20 μl of each ED sample was deposited at the bottom of the wells at a concentration equivalent to 5 μg of proteins per lane. Electrophoresis was carried out at 100 V, 50 mA (direct current) for 10 h in a vertical unit of gel plates (Hoefer Scientific Instr., San Francisco, Calif.). For the determinations of molecular weight, a kit intended for the calibration of low molecular weights )Pharmacia-Biotech, Saint-Quentin en Yvelines, France) was used. Staining with Coomasie R350 (Pharmacia-Biotech, France) was used for visualizing the bands on the polyacrylamide matrix, and silver staining (Tsai and Frasch, 1982 Anal. Biochem. 199, 115–119) was used for visualizing the LPS components.

Immunoblotting

The protein bands were transferred from the gel to an Immobilon® PVDF membrane (Millipore Corp., St Quentin en Yvelines, France) by electroblotting using a MiniTrans-Blot® electrophoresis transfer cell (BioRad) with a transfer buffer solution (Tris 25 mM; glycine 192 mM; methanol 20% v/v; pH=8.3) at 100 V, 250 mA for 1 hour. BioRad colloidal gold total protein stain was used for verifying the conditions of electrophoresis transfer and for identifying the protein bands on the membranes. After transfer, the membranes were immersed for 30 min in a blocking solution (gelatin 3% in Tris 20 mM and NaCl 0.5 M) and rinsed with gentle agitation in a washing solution (Tris 20 mM; NaCl, 0.5 M; Tween® 20 0.05%).

The membranes were then brought into contact with solutions of monoclonal antibodies diluted from 1/100 to 1/1000 in the antibody buffer (Tris 20 mM; NaCl 0.5 M; Tween® 20 0.05%; gelatin 1%) for 180 min at 25° C.

Fixation of the monoclonal antibodies to the peptide bands was visualized by means of alkaline phosphatases (PA) conjugated with anti-mouse goat immunoglobulins IgG (heavy and light chains) (BioRad, dilution to 1/2000) and using a substrate solution for PA (BioRad).

Figure 2:
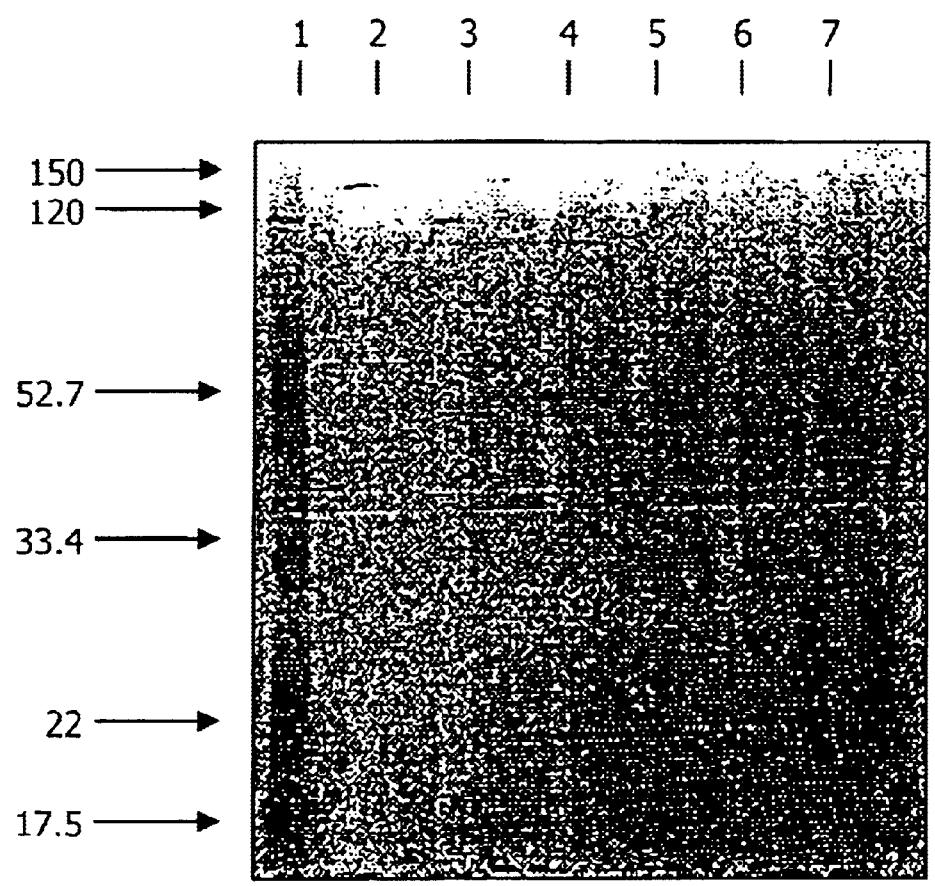

A positive serum obtained from mice immunized with a reference strain of *T. equigenitalis* and a negative serum from un-immunized mice were used as experimental controls. FIG. 2 shows an immunoblot between the bacterial proteins and the AcM according to the invention on the one hand and the positive mouse serum on the other hand.

The positive serum collected from immunized mice reacts with 5 proteins from strain R-19: 120 kDA; 52.7 kDA; 33.4 kDA; 17.5 kDA and 22 (LPS) kDA.

8 of the 14 monoclonal antibodies tested react positively and 6 of them negatively. The specific epitopes recognized by these 8 monoclonal antibodies reacting positively are:

150 kDa for monoclonal antibody 3B6.1,
120 kDa for monoclonal antibody 11C9.1,
52.7 kDa for monoclonal antibodies 7B8.1 and 7C4.10,
22 kDa (LPS) for monoclonal antibodies 7B7.10, 7D7.3, 11C9.4 and 11C9.5

These results are also shown in Table III, columns 5 and 8.

Dot-blotting

Immobilon® PVDF membranes (Sigma) were pre-moistened with a 100% methanol solution for 1 to 3 s, immersed in distilled water for 1–2 min to eluate the methanol and equilibrated in a washing solution (Tris 20 mM; NaCl 500 mM; Tween® 20 0.05%; pH=7.5). The EN and ED extracts were fixed to the membranes by incubation for 1 hour at ambient temperature. The dot membranes were washed twice for 10 min in the washing solution then immersed in the blocking solution (gelatin 3% in Tris 20 mM and NaCl 500 mM) for 1 hour. The membranes were washed twice as previously and incubated with the selected monoclonal antibodies in the same conditions as for immunoblotting.

Fixation of the monoclonal antibodies to the dot-blot membranes was detected by means of PA conjugated to anti-mouse goat immunoglobulins (heavy and light chains) and by means of a substrate solution for PA (BioRad).

The same sera, positive and negative controls were used as for immunoblotting.

To determine whether the negative results observed in immunoblotting are due to the fact that the epitopes were damaged by the denaturing reagents used for preparing the extracts, the 14 monoclonal antibodies were compared by dot-blot with the EN and ED extracts from strain R-19.

Figure 3:

FIG. 3 shows, in dot-blot, the R19 proteins that reacted in tracks 1 to 14 with the AcM in Table III, on track SP with the positive mouse serum and on track SN with the negative mouse serum. The results obtained are also presented in Table III, columns 6 and 7.

The 6 antibodies displaying a negative immunoblot also display a negative dot-blot with the denatured extracts from strain R-19 (Table III, columns 5 and 6). However, they display a positive dot-blot with the undenatured extracts (Table III, column 7).

In non-denaturing conditions (treatment with SDS only) the conformation and the activity of the proteins remain intact but in reducing conditions (treatment with β-mercaptoethanol and high temperatures), the conformation of certain proteins changes and the epitopes are destroyed. The absence of reactivity of the 6 monoclonal antibodies tested in immunoblot with strain R-19 is therefore very probably due to these changes in conformation and destruction of epitopes.

8 monoclonal antibodies which preserve their reactivity to bacterial extracts ED were therefore produced.

These 8 monoclonal antibodies may therefore be suitable reagents for detecting antigens of *T. equigenitalis* and, more particularly, for diagnosis of CEM. Antibodies of this kind can be used for characterizing bacteria of the genus Taylorella in any biological preparation using denaturing conditions.

Determination of the Isotype

For determination of the isotype of the monoclonal antibodies the immunotype kit from Sigma was used which consists of strips of nitrocellulose pre-covered with mouse immunoglobulin anti-isotype antibodies. After additional incubation, the identity of the immunoglobulin isotype is detected using a biotin-avidin-enzyine detection system.

The results obtained are shown in column 9 of Table III.

The 14 monoclonal antibodies produced form part of the IgM for 5 of them, of IgG2b for 4 of them, of IgG3 for 3 of them and of IgG1 for 2 of them.

Example 3

Comparative Test of Different Diagnostic Assays for CEM
  a) bacteriological culture of the bacterial flora
  b) detection by polyclonals and IIF
  c) detection by the invention which is the subject of the present Application: monoclonals and IIF.

For 1 month, 368 swabs from mares (clitoral fossa, cervix) and from stallions (pre-ejaculatory fluid, urethral fossa) were investigated by the two immunofluorescence techniques, the technique according to the memorandum of the Ministry of agriculture and fisheries (DGAL/SDSPA/N95/N°8037) with polyclonal antibodies and the technique according to the invention. The positives according to one of the two techniques were isolated by culture on agar media. 64 samples were found positive with the polyclonal antibodies and 17 with the monoclonal antibodies; no culture made it possible to isolate *T. equigenitalis* bacteria.

These results clearly demonstrate the greater specificity provided by the invention in this investigation.

Example 4

Other Comparative Test

A second test intended to compare the screening of CEM by bacteriological culture, by polyclonals and IIF and by the invention which is the subject of the present Application (monoclonals and IIF) was carried out on 1014 samples representing all the analysis requests.

1 *T. equigenitalis* was isolated by bacteriological culture (on 1014 samples), 58 fluorescences were established with the monoclonal antibodies according to the invention (6%) and 409 with polyclonal antibodies (40%).

The differences measured between the monoclonal and polyclonal antibodies are statistically significant, with a probability greater than 99.9% (Khi 2 test).

The screening by antibody and indirect immunofluorescence techniques, namely the "polyclonal antibodies" technique and the technique which is the subject of the present invention both detected the *T. equigenitalis* isolated by bacteriological culture.

The specificity of the monoclonal antibodies according to the invention, used in the context of indirect immunofluorescence, is greater than that of polyclonal antibodies (94% vs 60%).

Example 5

Elimination of Non "Antigen-antibody" Reactions

Non-specific reactions can sometimes be obtained between antibodies and *Staphylococcus* (*S. aureus*) and *Streptococci* (groups C and G). via proteins (protein A for *S. aureus* and protein G for the Streptococci of groups C and G). The reactions are not of antigen-antibody type.

Such non-specific reactions can be observed with the monoclonal antibodies according to the invention: in fact, 2 strains of bacteria known for producing proteins A and G (*Staphylococcus aureus*, Cowan strain and *Streptococci*, strain 26RP66) were subjected to the detection technique according to the invention, namely monoclonal antibodies and indirect immunofluorescence, and both produced a fluorescence (strain R-19 of *T. equigenitalis* was used as an experiment control).

In order to eliminate these non-specific reactions, a blocking technique was developed.

Monoclonal antibodies according to the invention conjugated with FITC, intended for a direct immunofluorescence detection were produced.

Two monoclonal antibodies according to the invention, one IgG2b (10C9.6) and one IgG3 (7C4.10) were concentrated 10 times by precipitation with ammonium sulphate and purified on a column of Protein A Sepharose (Pharmacia) by adsorption in a Tris 100 mM pH8 buffer and elution in a 100 mM glycine buffer pH3. The antibodies thus purified were labelled with gamma isomer FITC (fluorescein isothiocyanate) and the antibody-FITC conjugates were separated from the unlabelled molecules by being passed through a Sephadex G25 column (Pharmacia).

Three types of strip were prepared:

*T. equigenitalis* strain R-19 streptomycin resistant,

*Staphylococcus aureus*, Cowan strain,

Group C *Streptococcus*, strain 26RP66.

These strips were then subjected to blocking by incubation at 37° C. for 1 hour in a serum from which anti-*T. equigenitalis* antibodies have been removed. Three sera were compared: mouse serum, rabbit serum and human serum.

After washing with PBS and rinsing with distilled water, the plates were incubated for 1 hour at 37° C. with the monoclonal antibodies according to the invention labelled with FITC described above.

After final washing and rinsing, the strips are mounted in glycerin, buffered and examined under a fluorescence microscope.

These three blocking techniques show a fluorescence for *T. equigenitalis* plates and show no fluorescence for the non-specific bond strips (*S. aureus* and *Streptococcus*).

The best blocking was obtained with mouse serum.

It is therefore possible with the detection technique according to the present invention to eliminate non-specific reactions while retaining the specific antigen-antibody reaction.

This technique of blocking by serum from which anti-*T. equigenitalis* antibodies have been removed and direct immunofluorescence can advantageously be used for confirmation of the positive results obtained by the technique of indirect immunofluorescence and monoclonal antibodies according to the invention.

Example 6

Production of anti-*Taylorella equigenitalis* anti-antibodies

1. Production of anti-*T. equigenitalis* monoclonal antibodies (AcM1)

The procedure described above is followed.

2. Purification of the AcM1

The AcM1 are precipitated by adding saturated ammonium sulphate to a final concentration of 50%. After centrifugation, the precipitate is resuspended in PBS, then filtered on Sephadex® G75 gel (Pharmacia) and finally purified by affinity chromatography on a column of protein A-Sepharose® CL-4B.

3. Preparation of the Immunogen

The purified AcM1 are homopolymerized in the presence of glutaraldehyde at 0.25% for hours at 4° C. The reaction is stopped by adding a 0.2 M glycine buffer and the polymers are dialysed against PBS.

4. Immunization of Mice

BALB/C mice are immunized by 1 SC injection of a mixture of equal parts of 50 µg of polymerized AcM1 and complete Freund adjuvant. Two further injections are applied at intervals of 2 weeks, one with incomplete Freund adjuvant, and the other without adjuvant and by peritoneal route.

5. Production of anti-antibody Monoclonal Antibodies Against *T. equigenitalis*. (AcM2)

The procedure described above is followed.

6. Purification of Fab fragments of the AcM1

Fab fragments of the AcM1 antibodies are purified after digestion of the AcM1 by papain (incubation of the AcM1 for 45 min at 37° C. in a solution of papain, 2-β-mercaptoethanol, and 1.5 M EDTA at pH 8. The ratio is 10 μg of papain per mg of AcM1. Digestion is stopped by adding N-methylmaleimide 10 mM (Sigma). The undigested antibodies and the Fc fragments are eliminated by affinity chromatography on a column of protein A-Sepharose CL-4B® (Pharmacia). The purity of the Fab fragments is verified by SDS-PAGE.

7. Screening of AcM2-producing hybridomas by an ELISA assay Microplates (Maxisorb, Nunc) are incubated for 16 h at 4° C. with 100 μl/well of a suspension of 0.2 μg/ml of Fab in carbonate buffer pH 8. The microplates are washed 3 times with PBS-Tween 20® (0.05%), pH 7.2, then the nonspecific sites are blocked with a solution of BSA 2% in PBS-TWEEN 20® (phosphate buffered saline with 0.05% nonionic detergent Tween-Sigma, St. Louis Mo.). for 30 min at 37° C. After washing 3 times with PBS-Tween 20®, the hybridoma culture supernatants are incubated for 1 h at 37° C. After washing 3 times with PBS-Tween 20®, reaction is detected with an anti-mouse conjugate labelled with peroxidase and its substrate.

The hybridomas that are positive in the ELISA assay are selected and the supernatants are used for preparation of the vaccine.

8. Preparation of the Vaccine

The AcM2 antibodies of the selected hybridomas, then their corresponding Fab fragments are purified according to the methods described above.

The Fab fragments are coupled with keyhole limpet haemocyanin (KLH, Sigma) by incubation for 16 h at 4° C. in a 0.05% solution of glutaraldehyde (Sigma), in a 1/1 ratio. The reaction is stopped with a 0.02 M glycine solution and the conjugates are dialysed against PBS. The protein is dosed at 25–100 μg per dose of vaccine and aluminium hydroxide is added as adjuvant to the vaccine.

What is claimed is:

1. An isolated monoclonal antibody or its Fv, Fab or $F(ab')^2$ fragment, which recognizes a 150 kDA *T. equigenitalis* protein.

2. A method of obtaining a monoclonal antibody according to claim 1, comprising:

fusing non-secreting murine mycloma cells with spleen cells from mice immunized by means of a strain of the species *T. equigenitalis* or extract(s) from such a strain, screening hybridomas whose culture supernatants exhibit a positive reaction with a 150 kDA *T. equigenitalis* protein, selecting by cloning the hybridomas with respect to their reactivity, in relation to *T. equigenitalis,* recovering the monoclonal antibody, and optionally purifying said monoclonal antibody.

3. A strain of hybridoma, which secretes the monoclonal antibody according to claim 1.

4. An isolated monoclonal antibody or its Fv, Fab or $F(ab')^2$ fragment according to claim 1, in combination with an antibody or Fv, Fab or $F(ab')^2$ fragment thereof which recognizes a 120 kDA *T equigenitalis* protein.

5. An isolated monoclonal antibody or its Fv, Fab or $F(ab')^2$ fragment according to claim 1, combination with an antibody or Fv, Fab or $F(ab')^2$ fragment thereof which recognizes a 52.7 kDA *T. equigenitalis* protein.

6. An isolated monoclonal antibody or its Fv, Fab or $F(ab')^2$ fragment according to claim 1, in combination with an antibody or Fv, Fab or $F(ab')^2$ fragment thereof which recognizes a 22 (LPS) kDA *T. equigenitalis* antigen.

7. An isolated monoclonal antibody or its Fv, Fab or F(ab')² fragment according to claim 1, in combination with at least one antibody or Fv, Fab or F(ab')² fragment thereof which recognize *T. equigenitalis* antigens selected from the group consisting of *T. equigenitalis* antigens of 120 kDA, 52.7 kDA and 22 (LPS) kDA.

8. A method of identification of a bacterium of the species *T. equigenitalis* in a specimen or in a culture comprising:

bringing the specimen or the culture to be analyzed, which may contain *T. equigenitalis*, into contact with an effective quantity of the combination of an isolated monoclonal antibody or its Fv, Fab or F(ab')² fragment which recognizes a 150 kDA *T. epuigenitalis* protein and at least one antibody or Fv, Fab or F(ab')² fragment thereof which recognize *T. equigenitalis* antigen selected from the group consisting of *T. equigenitalis* antigens of 120 kDA, 52.7 kDA and 22 (LPS) kDA according to claim 7, under conditions permitting a reaction of the antigen-antibody type, and detecting any antigen/antibody type reaction product formed, wherein said product is indicative of the presence of a bacterium of the species *T. equigenitalis*.

9. A method of diagnosis of an infection by *T. equigenitalis* comprising:

(a) bringing the combination of an isolated monoclonal antibody or its Fv, Fab or F(ab')² fragment which recognizes a 150 kDA *T. equigenitalis* protein and at least one antibody or Fv, Fab or F(ab')² fragment thereof which recognize *T. equigenitalis* antigens selected from the group consisting of *T. equigenitalis* antigens of 120 kDA, 52.7 kDA and 22(LPS) kDA according to claim 7 into contact with a biological sample, wherein said sample may contain *T. equigenitalis* antigen, under conditions permitting an antigen-antibody reaction, and (b) detecting any antigen/antibody type reaction product formed in said sample between the antibody or fragment of (a) and a *T. equigenitalis* antigen, wherein said product is indicative of a diagnosis for *T. equigenitalis* infection.

10. A kit for application of a method of identification of a bacterium of the species *T. equigenitalis* in a specimen or in a culture comprising:

the combination of an isolated monoclonal antibody or its Fv, Fab or F(ab')² fragment which recognizes a 150 kDA *T. equigenitalis* protein and at least one antibody or Fv, Fab or F(ab')² fragment thereof which recognize *T. equigenitalis* antigens selected from the group consisting of *T. equigenitalis* antigens of 120 kDA, 52.7 kDA and 22 (LPS) kDA according to claim 7, reagents for detecting the intended immunologic reaction, optionally, reagents for blocking the non antigen-antibody reactions, and instructions for use.

11. A method of identification of a bacterium of the species *T. equigenitalis* in a specimen or in a culture comprising:

bringing the specimen or the culture to be analyzed, which may contain *T. equigenitalis* antigen, into contact with an effective quantity of a monoclonal antibody or Fv, Fab or F(ab')² fragment thereof according to claim 1, under conditions permitting a reaction of the antigen-antibody type, and detecting any antigen/antibody type reaction product formed wherein said product is indicative of the presence of a bacterium of the species *T. equigenitalis*.

12. The method according to claim 11, further comprising blocking the non antigen-antibody reactions.

13. The method according to claim 12, wherein the blocking comprises saturating the specimen with serum from which anti-*T. epuigenitalis* antibodies have been removed.

14. A method of diagnosis of an infection by *T. equigenitalis* comprising:

(a) bringing a monoclonal antibody or fragment thereof according to claim 1, into contact with a biological sample, wherein said sample may contain *T. equigenitalis* antigen, under conditions permitting an antigen-antibody reaction, and (b) detecting any antigen/antibody type reaction product formed in said sample between the antibody or fragment of (a) and a *T. equigenitalis* antigen, wherein said product is indicative of a diagnosis for *T. equigenitalis* infection.

15. The method according to claim 14, further comprising blocking the non antigen-antibody reactions.

16. A kit for application of a method of identification of a bacterium of the species *T. equigenitalis* in a specimen or in a culture comprising:

a monoclonal antibody or fragment according to claim 1, a reagent for detecting the intended immunologic reaction, optionally, a reagent for blocking the non antigen-antibody reactions, and instructions for use.

17. A kit according to claim 16, wherein said reagent for detecting the intended immunologic reaction is selected from the group consisting of markers and buffers.

18. A kit according to claim 16, wherein a reagent for blocking the non antigenic-antibody reaction is included and said reagent is mouse serum.

19. An isolated monoclonal antibody or its Fv, Fab or F(ab')² fragment according to claim 1, in combination with antibodies or Fv, Fab or F(ab')² fragments thereof which recognize *T. equigenitalis* antigens of 120 kDA, 52.7 kDA and 22 (LPS) kDA.

20. A method of identification of a bacterium of the species *T. equigenitalis* in a specimen or in a culture comprising:

bringing the specimen or the culture to be analyzed, which may contain *T. equigenitalis*, into contact with an effective quantity of the combination of an isolated monoclonal antibody or its Fv, Fab or F(ab')² fragments which recognizes a 150 kDA *T. equigenitalis* protein and antibodies or Fv, Fab or F(ab')² fragments thereof which recognize *T. eguigenitalis* antigens of 120 kDA, 52.7 kDA and 22 (LPS) kDA according to claim 19, under conditions permitting a reaction of the antigen-antibody type, and detecting any antigen/antibody type reaction product formed, wherein said product is indicative of the presence of a bacterium of the species *T. equigenitalis*.

21. A method of diagnosis of an infection by *T. equigenitalis* comprising:

(a) bringing the combination of an isolated monoclonal antibody or its Fv, Fab or F(ab')² fragment which recognizes a 150 kDA *T. equigenitalis* protein and antibodies or Fv, Fab or F(ab')² fragments thereof which recognize *T. equigenitalis* antigens selected from the group consisting of *T. equigenitalis* antigens of 120 kDA, 52.7 kDA and 22(LPS) kDA according to claim 19, into contact with a biological sample, wherein said sample may contain *T. equigenitalis* antigen, under conditions permitting an antigen-antibody reaction, and (b) detecting any antigen/antibody type reaction product formed in said sample between the antibody or fragment of (a) and a *T. equigenitalis* antigen, wherein said product is indicative of a diagnosis for *T. equigenitalis* infection.

22. A kit for application of a method of identification of a bacterium of the species *T. equigenitalis* in a specimen or in a culture comprising:

the combination of an isolated monoclonal antibody or its Fv, Fab or F(ab')$^2$ fragment which recognizes a 150 kDA *T. equigenitalis* protein and antibodies or Fv, Fab or F(ab')$^2$ fragments thereof which recognize *T. eguigenitalis* antigens selected from the group consisting of *T. equigenitalis* antigens of 120 kDA, 52.7 kDA and 22 (LPS) kDA according to claim 19, reagents for detecting the intended immunologic reaction, optionally, reagents for blocking the non antigen-antibody reactions, and instructions for use.

23. An isolated monoclonal antibody obtained by a process comprising:

fusing non-secreting murine myeloma cells with spleen cells from mice immunized against an inactivated strain of the species *T. equigenitalis* or extract(s) of such a strain, cloning and selecting according to the capacity of their culture supernatant to recognize a 150 kDA *T. equigenitalis* protein, recovering the required monoclonal antibody, and optionally purifying said monoclonal antibody.

24. An isolated monoclonal antibody or its Fv, Fab or F(ab')$^2$ fragment according to claim 23, in combination with an antibody or Fv, Fab or F(ab')$^2$ fragment thereof which recognizes a 120 kDA *T. equigenitalis* protein.

25. An isolated monoclonal antibody or its Fv, Fab or F(ab')$^2$ fragment according to claim 23, in combination with an antibody or Fv, Fab or F(ab')$^2$ fragment thereof which recognizes a 52.7 kDA *T. equigenitalis* protein.

26. An isolated monoclonal antibody or its Fv, Fab or F(ab')$^2$ fragment according to claim 23, in combination with an antibody or Fv, Fab or F(ab')$^2$ fragment thereof which recognizes a 22 (LPS) kDA *T. equigenitalis* antigen.

27. A strain of hybridoma, which secretes the monoclonal antibody according to claim 23.

28. A method of identification of a bacterium of the species *T. equigenitalis* in a specimen or in a culture comprising:

bringing the specimen or the culture to be analyzed, which may contain *T. equigenitalis* antigen, into contact with an effective quantity of the monoclonal antibody or Fv, Fab or F(ab')$^2$ fragment thereof according to claim 23, under conditions permitting a reaction of the antigen-antibody type, and detecting any antigen/antibody type reaction product formed, wherein said product is indicative of the presence of a bacterium of the species *T. equigenitalis*.

29. A method of diagnosis of an infection by *T. equigenitalis* comprising:

(a) bringing the combination of an isolated monoclonal antibody or its Fv, Fab or F(ab')$^2$ fragment which recognizes a 150 kDA *T. eguigenitalis* protein and antibodies or Fv, Fab or F(ab')$^2$ fragments thereof which recognize *T. eguigenitalis* antigens selected from the group consisting of *T. equigenitalis* antigens of 120 kDA, 52.7 kDA and 22 (LPS) kDA according to claim 23 into contact with a biological sample, wherein said sample may contain *T. equigenitalis* antigen, under conditions permitting an antigen-antibody reaction, and (b) detecting any antigen/antibody type reaction product formed in said sample between the antibody or fragment of (a) and a *T. equigenitalis* antigen, wherein said product is indicative of a diagnosis for *T. equigenitalis* infection.

30. A kit for application of a method of identification of a bacterium of the species *T. equigenitalis* in a specimen or in a culture comprising:

a monoclonal antibody or fragment according to claim 23, reagents for detecting the intended immunologic reaction, optionally, reagents for blocking the non antigen-antibody reactions, and instructions for use.

31. An isolated monoclonal antibody or its Fv, Fab or F(ab')$^2$ fragment according to claim 23, in combination with at least one antibody or Fv, Fab or F(ab')$^2$ fragment thereof which recognizes a *T. equigenitalis* antigen selected from the group consisting of *T. equigenitalis* antigens of 120 kDA, 52.7 kDA and 22 (LPS) kDA.

32. A method of identification of a bacterium of the species *T. equigenitalis* in a specimen or in a culture comprising:

bringing the specimen or the culture to be analyzed, which may contain *T. equigenitalis*, into contact with an effective quantity of the combination of an isolated monoclonal antibody or its Fv, Fab or F(ab')$^2$ fragment which recognizes a 150 kDA *T. epuigenitalis* protein and at least one antibody or Fv, Fab or F(ab')$^2$ fragment thereof which recognizes *T. equigenitalis* proteins of 120 kDA, 52.7 kDA and 22 (LPS) kDA according to claim 31, under conditions permitting a reaction of the antigen-antibody type, and detecting any antigen/antibody type reaction product formed, wherein said product is indicative of the presence of a bacterium of the species *T. equigenitalis*.

33. A method of diagnosis of an infection by *T. equigenitalis* comprising:

(a) bringing the combination of an isolated monoclonal antibody or its Fv, Fab or F(ab')$^2$ fragment which recognizes a 150 kDA *T. equigenitalis* protein and at least one antibody or Fv, Fab or F(ab')$^2$ fragment thereof which recognize *T. equigenitalis* antigens selected from the group consisting of *T. equigenitalis* antigens of 120 kDA, 52.7 kDA and 22 (LPS) kDA according to claim 31, into contact with a biological sample, wherein said sample may contain *T. equigenitalis* antigen, under conditions permitting an antigen-antibody reaction, and (b) detecting any antigen/antibody type reaction product formed in said sample between the antibody or fragment of (a) and a *T. equigenitalis* antigen, wherein said product is indicative of a diagnosis for *T. equigenitalis* infection.

34. A kit for application of a method of identification of a bacterium of the species *T. equigenitalis* in a specimen or in a culture comprising:

the combination of an isolated monoclonal antibody or its Fv, Fab or F(ab')$^2$ fragment which recognizes a 150 kDA *T. equigenitalis* protein and at least one antibody or Fv, Fab or F(ab')$^2$ fragment thereof which recognize

*T. equigenitalis* antigens selected from the group consisting of *T. eguigenitalis* antigens of 120 kDA, 52.7 kDA and 22 (LPS) kDA according to claim 31, reagents for detecting the intended immunologic reaction, optionally, reagents for blocking the non antigen-antibody reactions, and instructions for use.

35. An isolated monoclonal antibody or its Fv, Fab or F(ab')$^2$ fragment according to claim 23, in combination with antibodies or Fv, Fab or F(ab')$^2$ fragments thereof which recognize *T. equigenitalis* antigens of 120 kDA, 52.7 kDA and 22 (LPS) kDA.

36. A method of identification of a bacterium of the species *T. equigenitalis* in a specimen or in a culture comprising:

bringing the specimen or the culture to be analyzed, which may contain *T. equigenitalis*, into contact with an effective quantity of the combination of an isolated monoclonal antibody or its Fv, Fab or F(ab')$^2$ fragment which recognizes a 150 kDA *T. equigenitalis* protein and antibodies or Fv, Fab or F(ab')$^2$ fragments thereof which recognize *T. equigenitalis* antigens of 120 kDA, 52.7 kDA and 22 (LPS) kDA according to claim 35, under conditions permitting a reaction of the antigen-antibody type, and detecting any antigen/antibody type reaction product formed, wherein said product is indicative of the presence of a bacterium of the species *T. equigenitalis*.

37. A method of diagnosis of an infection by *T. equigenitalis* comprising:

(a) bringing the combination of an isolated monoclonal antibody or its Fv, Fab or F(ab')$^2$ fragment which recognizes a 150 kDA *T. equigenitalis* protein and antibodies or Fv, Fab or F(ab')$^2$ fragments thereof which recognize *T. equigenitalis* antigens of 120 kDA, 52.7 kDA and 22 (LPS) kDA according to claim 35 into contact with a biological sample, wherein said sample may contain *T. equigenitalis* antigen, under conditions permitting an antigen-antibody reaction, and (b) detecting any antigen/antibody type reaction product formed in said sample between the antibody or fragment of (a) and a *T. equigenitalis* antigen, wherein said product is indicative of a diagnosis for *T. equigenitalis* infection.

38. A kit for application of a method of identification of a bacterium of the species *T. equigenitalis* in a specimen or in a culture comprising:

the combination of an isolated monoclonal antibody or its Fv, Fab or F(ab')$^2$ fragment which recognizes a 150 kDA *T. equigenitalis* protein and antibodies or Fv, Fab or F(ab')$^2$ fragments thereof which recognize *T. equigenitalis* antigens selected from the group consisting of *T. equigenitalis* antigens of 120 kDA, 52.7 kDA and 22 (LPS) kDA according to claim 35, reagents, for detecting the intended immunologic reaction, optionally, reagents for blocking the non antigen-antibody reactions, and instructions for use.

* * * * *